US00RE44159E

(19) United States
(12) Reissued Patent
Spona et al.

(10) Patent Number: US RE44,159 E
(45) **Date of Reissued Patent: *Apr. 16, 2013**

(54) COMPOSITION FOR CONTRACEPTION

(75) Inventors: Jurgen Spona, Vienna (AT); Bernd Dusterberg, Berlin (DE); Frank Ludicke, Basel (CH)

(73) Assignee: Bayer Schering Pharma Aktiengesellschaft, Berlin (DE)

( * ) Notice: This patent is subject to a terminal disclaimer.

(21) Appl. No.: 11/892,969

(22) Filed: Aug. 28, 2007

Related U.S. Patent Documents

Reissue of:
(64) Patent No.: 5,824,667
Issued: Oct. 20, 1998
Appl. No.: 08/742,147
Filed: Oct. 31, 1996

U.S. Applications:
(60) Division of application No. 10/916,600, filed on Aug. 12, 2004, now abandoned, which is a continuation of application No. 10/193,758, filed on Jul. 12, 2002, now abandoned, which is a continuation of application No. 09/504,084, filed on Feb. 15, 2000, now Pat. No. Re. 37,838, which is a continuation of application No. 08/268,996, filed on Jun. 30, 1994, now Pat. No. 5,583, 129, application No. 11/892,969, which is a continuation of application No. 09/503,952, filed on Feb. 15, 2000, now Pat. No. Re. 37,564, which is a continuation of application No. 08/268,996, filed on Jun. 30, 1994, now Pat. No. 5,583,129.

(30) Foreign Application Priority Data

Dec. 22, 1993 (DE) ..... P 43 44 462

(51) Int. Cl.
*A61K 31/565* (2006.01)
*A61K 31/585* (2006.01)

(52) U.S. Cl.
USPC ..... 514/170

(58) Field of Classification Search ..... None
See application file for complete search history.

(56) References Cited

U.S. PATENT DOCUMENTS

| | | | | |
|---|---|---|---|---|
| 3,639,600 | A | 2/1972 | Hendrix | |
| 3,932,635 | A | 1/1976 | Segre | |
| 3,939,264 | A | 2/1976 | Lachnit-Fixson | |
| 3,969,502 | A | 7/1976 | Lachnit-Fixson et al. | |
| 4,129,564 | A | 12/1978 | Wiechert et al. | |
| 4,145,416 | A | 3/1979 | Lachnit-Fixson et al. | |
| 4,826,831 | A | 5/1989 | Plunkett et al. | |
| 4,904,462 | A | 2/1990 | Schulze et al. | |
| 5,010,070 | A | 4/1991 | Boissonneault | |
| 5,098,714 | A | 3/1992 | Wright | |
| 5,108,995 | A | 4/1992 | Casper | |
| 5,208,225 | A | 5/1993 | Boissonneault et al. | |
| 5,256,421 | A | 10/1993 | Casper | |
| 5,262,408 | A | 11/1993 | Bergink | |
| 5,340,584 | A * | 8/1994 | Spicer et al. | 424/426 |
| 5,418,228 | A | 5/1995 | Bennink | |
| 5,422,119 | A | 6/1995 | Casper | |
| 5,552,394 | A | 9/1996 | Hodgen | |
| 5,569,652 | A | 10/1996 | Beier et al. | |
| 5,583,129 | A | 12/1996 | Spona et al. | |
| 5,756,490 | A | 5/1998 | Lachnit et al. | |
| 2001/0056086 | A1 | 12/2001 | Habenicht | |

FOREIGN PATENT DOCUMENTS

| | | |
|---|---|---|
| AU | 55094/90 B | 11/1990 |
| CA | 2016780 | 7/2000 |
| DE | 30 22 337 A1 | 1/1982 |
| DE | 4 344 462 | 12/1993 |
| DE | 44 11 585 A1 | 10/1995 |
| EP | 0 253 607 | 1/1988 |
| EP | 0 398 460 B1 | 11/1990 |
| EP | 0 491 415 | 6/1992 |
| EP | 0 491 438 | 6/1992 |
| EP | 640 343 | 3/1995 |
| EP | 0 917 466 | 7/1997 |
| EP | 1 462 107 | 3/2003 |
| EP | 0 814 803 | 10/2006 |
| EP | 1 334 725 | 2/2007 |
| WO | WO 88/00469 | 1/1988 |
| WO | WO 95/26730 | 10/1995 |
| WO | WO 98/04246 | 2/1998 |
| WO | WO 98/04265 | 2/1998 |
| WO | WO 98/04267 | 2/1998 |
| WO | WO 98/04268 | 2/1998 |
| WO | WO 98/04269 | 2/1998 |

OTHER PUBLICATIONS

The Merck Manual, 17th edition (1999), pp. 1973-74; 1932.*
Cianci et al., Minerva Ginecol. (abstract), (Aug. 2007), 59(4), pp. 415.25.*
Kase, NG, Gender Medicine, (2009), 6, Part 1: 37-59.*
Translation of Minulet®, 1992 du Vidal.
Translation of Monevat®, 1992 du Vidal.
Translation of Szapiro, C.R.Ther.Pharmacol.Clin., 112, 1993, 3-7.
["Corrected Citation"]: Ansbacher, Contraception, 43(2), 1991, 139-147.
["Corrected Citation"]: Nardi et al., ActaEur.Fertil. 6(2), 1975, 153-165. (Abstract).
Spona et al., "*Gynecol Obstet Invest*", 23, pp. 184-193, (1987).
Jandrain et al., "*Am J. Obstet Gynecol*", 163, pp. 378-381, (1990).
Porcile et al., "*Fertility and Sterility*", 55, pp. 877-881, (Abstract only) (1991).
Oelkers et al., "*Acta Endocrinologica*", Suppl. 4, p. 71, #97, (1992) (Abstract only).
Scheen et al., "*Fertility and Sterility*", 59, pp. 797-802, (Abstract only) (1993).
Kuhnz et al., "*Contraception*", 48, pp. 557-575, (1993).
Foster, Low-dose Monophasic and Multiphasic Oral Contraceptives: A Review of Potency, Efficacy, and Side Effects, 7(3), 1989, 205-212.
Ansbacher, Contraception, 43(2), 1991, 365-371.
Zacur et al., Current Opinion in Obstetrics and Gynecology, 4, 1991, 365-371.
Smith et al., Clinical Pharmacy, 3, 1984, 485-496.
Fruzetti et al., Contraception, 63, 2001, 303-307.
Bachmann et al., Contraception, 70, 2004, 191-198.
Nappi et al., Contraception, 67, 2003, 355-359.

(Continued)

*Primary Examiner* — Phyllis G. Spivack
(74) *Attorney, Agent, or Firm* — Millen, White, Zelano & Branigan, PC

(57) ABSTRACT

A combination product for oral contraception is disclosed comprising an estrogen selected from
2.0 to 6.0 mg of 17β-estradiol and
0.020 mg of ethinylestradiol;
and a gestagen selected from
0.25 to 0.30 mg of drospirenone and
0.1 to 0.2 mg of cyproterone acetate,
followed by 5 or 4 pill-free or sugar pill days.

18 Claims, 1 Drawing Sheet

OTHER PUBLICATIONS
Spielmann et al., Eur.J.Contracep.Repr.Health Care, 4(suppl 2), 1999, 9-15.
Spielmann et al., Eur.J.Contracep.Repr.Health Care, 4(suppl 2), 1999, 17-25.
Oosterbaan, Eur.J.Contracep.Repr.Health Care, 4(suppl 2), 1999, 3-8.
Kuhl, Gynäkologe, 25, 1992, 231-240.
Elstein, Advances in Contraception, 10, 1994, 1-4.
Minulet®, 1992 du Vidal.
Moneva®, 1992 du Vidal.
Szapiro, C.R.Ther.Pharmacol.Clin, 112, 1993, 3-7.
Nardi et al., ActaEur.Fertil. 6(2), 1975, 153-165.
Serlaly D.: "The 20 mcg ethinylestadiol and 140 mcg Desogestrell pill: sic months, multicenter study in 235 Women," 2990, June *Fertil. Contracept.Sex,* 18(6): 407-12.
Tuimala R. et al.: "A Clinical comparison in Finland of two oral contraceptives containing 0,150 mg Desogestrel in combination with 0,020 mg or 0,030 mg ethinyiestradil," *Acta Obstet Gynecol Scand Suppl*, 1987, 1477:7-12.
Kaplan, *Cardiol.Clin.* 6:475-482 (1988).
Johnson, Clin.Obst. And Gynecol., 30:267-276 (1987).
Elstein, M.,: "Consensus paper—Low dose contraceptive formulations: is further reduction in steroid dosage justified?" *Advances in Contraception*, 1994; 10:1-4.
Kuhl, H.,: "Recent developments in hormonal contraception," *Gynakologe* (1992) 25: 231-240. (translation).
Translation of EP 0398460 A2, Application No. 90250127.9, filed May 16, 1990; (pub. Nov. 1990).
Translation of DE 3022337. (Jan. 1982).
Nardi, M. et al, "Cyproterone Acetate—Ethinylestradiol Treatment of Hirsutism, Acne, Seborrhea and Alopecia," *Insegnamento di Endocrinologia Ginecologica,* Acta Eur. Fertil 6(2), Apr. 20, 1975, pp. 153-165.
Excerpts (D7) from opposition to corresponding German patent 4344462; cited in oppositions against corresponding EP patent 735883.
Patent and Utility Model filed Dec. 22, 1993, re DE 4344462, translation pp. 22-23.
G.B. Melis, et al., Contraception, A*A Comparative Study on the Effects of a Monophasic Pill Containing Desogestrel Plus 20 Φg Ethinylestradiol, a Triphasic Combination Levonorgestrel and a Monophasic Combination Containing gestrodene on Coagulatory Factors@,* vol. 43, No. 1, pp. 23-30 (Jan. 1991), [including abstract].
A.R. Genazzani, et al. (Ed), Progress in Gynecology and Obstetrics, A*Multicenter Clinical Trial on the new Oral Contraceptive Containing 20 Φg Ethinylestradiol@*, Chapter 1, pp. 747-756, (1990).
W. Oelkers et al., A*Journal of Clinical Endocrinology and Metabolism@*, p. 73, pp. 837-842, (1991).
W. Oelkers et al., AA*cta Endocrinologica@*, Suppl. 4, p. 71, #97, (1992) (Abstract Only).
W. Oelkers et al., A*Journal of Clinical Endocrinology and Metabolism@,* 80, pp. 1816-1821, (1995).
Elstein et al., *Zentralblatt für Gynäkologie@,* pp. 559-565, (1995).
Schillinger et al., A*Arzneim.-Forsch.@,* 26, pp. 2242-2245, (Abstract only), (1976).
Huempel et al., *Contraception@,* 16, pp. 199-216 (Abstract only), (1977).
Düsterberg et al., A*Acta Obstet Gynecol Scand, Suppl.@,* pp. 27-31, (1979).
Leis et al., A*Geburtshilfe Frauenheilkd@,* 39, pp. 54-57 (Abstract only), (1979).
Duesterberg et al., A*Acta Obstet Gynecol Scand Suppl@,* (88), pp. 27-31, (1979).
Klebe et al, A*Arch Gynecol@,* 234, pp. 113-120, (Abstract only) (1983).
Holdaway et al., A*Acta Endocrinol@,* 109, 522-529, (Abstract only) (1985).
Kuhl et al., A*Contraception@,* 30, pp, 467-482, (1985).
Larsson-Cohn et al., A*Acta Obstet Gynecol Scand@,* 65, pp. 125-128, (Abstract only) (1986).
Calaf-Alsina et al., A*Obstet Gynecol@,* 69, pp. 255-258, (Abstract only) (1987).
M. Elstein, A*Advances in Contraception@,* 12, pp. 155-156, (1996).
Foidart et al., A*Int=l J. Gynecol & Obstet@,* 46, Suppl. 3, p. 11, (1994).
0elkers et al., A*Advances in Contraception@,* 7, Suppl. 3, pp. 195-206 (1991).
J. Guillebaud, *Br. J. Family Planning,* 12 (Stippl.), 35-43 (1987).
Van Keep et al., eds. A*The Controversial Climactoric@,* MTP Press Limited, 9-18 (1981).
German Pharmacopeia, 9th Edition, 1986—English Translation.
Bilotta et al., "Multicenter clinical trial on the new oral contraceptive containing 20 μg ethinylestradiol," Progress in Gynecology and Obstetrics, Mar. 1989, pp. 747-756.
Petersen et al., "Effects of monophasic low-dose oral contraceptive on fibrin formation and resolution in young women," Hemostatic balance during oral contraception, Am. J. Obstet. Gynecoll, vol. 168, No. 1, part 1, pp. 32-38, Jan. 1993.
Fioretti et al., "Clinical and metabolic study of a new pill containing 20 mcg Ethinylestradiol plus 0.150 mg Desogestrel," Contraception, 1987, vol. 35, No. 3, pp. 229-243.
Losert et al., "Progestogens with Antimineralocorticold Activity," Arzneim.-Forsch./ Drug Res. 35, 1985, No. 2, pp. 459-471.
Wang et al., "Treatment of premenstrual sydrome by spironolactone: A double-blind, placebo-controlled study," Acta Obstet.Gynecol. Scand., 74: 803-808 (1995).
Muhn, P. et al., "Drosplrenone: A Novel Progestogen with Antimineralocorticoid and Antiandrogenic Activity," Annals New York Acad. Sciences, 761:311-35 (1995).
Nickisch et al., "Aldosterone Antagonists. 4. Synthesis and Activities of Steroidal 6,6-Ethylene-15,16-methylene 17-Spiroiactones," J.Med.Chem., 34:2964-2968 (1991).
Laurent, H. et al., "Synthesis and Activities of Anti-Aldosterones," Steroid Biochem., 19:771-776 (1983).
Casals-Stenzel, J. et al., "The Renal Action of Spriorenone and other 6β,7β; 15β, 16β-dimethylene-17-spriolactones, a new type of steriodal aldosterone antagonists," Arzeneim.-Forsch./Drug Res. 34:241-246 (1984).
Pollow, K. et al, "Dihydrospirorenone (ZK30595): A Novel Progestagen—Characterization of Binding to Different Receptor Proteins," Contraception 46:561-754 (1992).
McInnes et al., J. Clinical Pharmacology, 22:410-17, 410-11, 1982.
K. Fotherby, *Contraception*, 54:59-69, 61, 1996.
J.C. Chaumeil, Meth, Find Exp. Clin, Pharm., 20(3):211-215, 211, 1998.
Hess et al., Acta Pharmaceutica Technologica, 21(4) :245-54, 254, 1975.
Shah et al., Pharm. Tech. 152-60, 152, 1994.
Spona et al., "Shorter pill-free interval in combined oral contraceptives decreases follicular development" Contraception 54, 71-77, 1996.
J.O. Drife, "Oral contraception for the over 40s," Annual Progress in Reproductive Medicine, 1993.
Fitzgerald et al., "A comparison of the effects oftwo monophasic lo dose oral contraceptives on the inhibition of ovulation," Advances in Contraception 10, 5-18, 1994.
Endrikat et al., "A twelve-month comparative clinical investigation of two lo-dose oral contraceptives containing 20 μg ethinylestradiol / 75 μg gestodene and 30 μg ethinylestradiol / 75 μg gestodene, with respect to efficacy, cacyle control, and tolerance," Contraception 55, 131-137, 1997.
Sullivan et al., "Effect of 21-day and 24-day oral contraceptive regimens containing gestodene (60 μg (and ethinyl estradiol (15 μg) on ovarian activity," Fertility and Sterility 72, 1, 115-120, 1999.
Endrikat et al., "Double-blind, multicenter comparison of efficacy, cycle control, and tolerability of a 23-day versus a 21-day low-dose oral contraceptive regimen containing 20 μg ethinyl estradiol and 75 μg gestodene," Contraception 69, 2, 99-105, 2001.
Elomaa et al., "Ovulatory potential of preovulatory sized follicles during oral contraceptive treatment," Contraception 60, 275-279, 1999.

Krattenmacher et al., "Effects of drospirenone on blood pressure and heart rate in rats measured by highly sensitive radio-telemetry," XVII Meeting I.S.G.S.H. Nov. 25-28, 1995, p. 55.
Filshie et al., (ed.); Book: Contraception: Science and Practice; Chapter: Practical Prescribing of the Combined Oral Conraceptive Pill; Section: The Paramount Importance of the Pill-free Interval; Butterworth-Heinemann, pp. 76-82, 1989.
German Pharmacopeia, 9th Edition, 1986—English Translation, p. 105.
Martindale, The Extra Phamacopoeia, Edited by James E.F. Reynolds, pp. 2003-2004, Thirtieth Ed. (1993).
AHFS Drug Information 33, p. 2348, (1993).
Drug Information of the Health Care Professional, vol. 1, USP DI 1993, 13th Edition, Chapter 50.
Pearlstein et al., "Treatment of premenstrual dysphoric disorder with a new drospirenone—containing oral contraceptive formulation." Presented at the 60th Annual Meeting of the American Society for Reproductive Medicine, Philadelphia, PA, Oct. 20, 2004, pp. 1-26.
Filshie et al. (ed.); Book: Contraception: Science and Practice; Chapter: Practical Prescribing of the Combined Oral Contraceptive Pill; Section: The Paramount Inportance of the Pill-free Interval; Butterworth-Heinemann, pp. 76-82, 1989.
Chemical Abstracts 76:30782, Craft et al., 1971.
Facts & Comparisons, (1985), pp. 108c-108e.
Lammers et al., Acta Obstet. Gynecol. Scand., 70(6), pp. 497-500 (1991).
Archives of Gynecology and Obstetrics vol. 245, No. 1-4, 1989.
Elger et al., "Conception and pharmacodynamic profile of drospirenone." (Steroids) 2003, 891-905, 68.
Gladwell, M. "John Rock's Error." (The New Yorker). Mar. 13, 2000, 52-63.
Sulak, P.J., et al., "Extended Regimen Oral Contraceptives—Practical Management," Clinical Update—Supplemental to OBG Management, Jan. 2007, S1-S8.
Willis, S.A., et al., "Greater inhibition of the pituitary—ovarian axis in oral contraceptive regimens with a shortened hormone-free interval," Contraception 74(2006), pp. 100-103.
Hayes, J.L., et al., "A Pilot Clinical Trial of Ultrasound-Guided Postplacental Insertion of Levonorgestrel IUS," Contraception/Family Planning, vol. 107, No. 4 (Supplement), Apr. 2006—1 page.
Notice of Certification Under 21 U.S.C. § 355(j)(2)(B) (§ 505(j)(B)) of Federal Food, Drug and Cosmetic Act) and 21 C.F.R. § 314.95)—Sandoz Inc.'s Drospirenone; Ethinyl Estradiol Tablet, 3 mg; 0.02 mg—Sandoz Inc.'s ANDA 79-221, pp. 1-43.
Dinger, J., et al., Abstract #236, p. S104, Abstracts of the 24th ICPE, Pharmaco-epidemiology and Drug Safety 2008: 17: SI-S294.
Runnebaum, B et al., "New progestogens in oral contraceptives," Am J Obstet Gynecol, Oct. 1987, vol. 157, pp. 1059-1063.
Kuhl, H., "Pharmacokinetics of oestrogens and progestogens," Maturitas, 1990, vol. 12, pp. 171-197.
Bayer Healthcare, Patient Information Booklet for Angeliq film coated tablets, May 2008, pp. 1-12.
Kilogest, Consumer Medicine Information, Dec. 2006, pp. 1-3.
Landgren, B. M. et al., "The effect on follicular growth and luteal function of 'missing the pill': A comparison between a monophasic and a triphasic combined oral contraceptive," Contraception, Feb. 1991, vol. 43, No. 2, pp. 149-159.
Killick, S. R. et al., "Extending the duration of the pill-free interval during combined oral contraception," Advances in Contraception, 1990, vol. 6, pp. 33-40.
Letterie, G. S., Effect of "Missed" Pills on Oral Contraceptive Effectiveness, Jun. 1992, vol. 79, No. 6, pp. 979-982.
Shaw, Geoffrey et al., "Assessment of ovarian activity in a gestodene containing triphasic oral contraceptive," the British Journal of Family Planning, 1992, vol. 18, pp. 76-78.
Bye, P. et al., "'Missed Pill' conception: fact or fiction?" Bristish Medical Journal, Jun. 22, 1985, vol. 290, pp. 1905.
Brenner, P. F. et al., "Serum levels of d-norgestrel, luteinizing hormone, follicle-stimulating hormone, estradiol, and progesterone in women during and following ingestion of combination oral contraceptives containing dl-norgestrel," Am J Obstet Gynecol, Sep. 15, 1977, pp. 133-140.
Molley et al., "'Missed Pill' conception: fact of fiction?" British Medical Journal, vol. 290, May 18, 1985, pp. 1474-1475.
Andreasen, E. E. et al., "Progesterone and gestagen treatment. Pharmacologic and clinical aspects," Ugeskrift for Laeger, Aug. 7, vol. 151, No. 32, pp. 2021-2026 Abstract only.
Spona, J. et al., "Pharmacological and endocrine profiles of gestodene," Int. J. Fertil., 1987, 32 Suppl: 6-14.
Spona, J et al., "Inhibition of ovulation by a triphasic gestodene-containing oral contraceptive," Advances in Contraception, 1993, vol. 9, pp. 187-194.
Nakajima, S. J. et al., "Efficacy and safety of a new 24-day oral contraceptive regimen of norethindrone acetate 1 mg/ethinyl estradiol 20 μg (Loestrin 24 Fe)," Contraception, 2007, vol. 75, pp. 16-22.
Schneider, W. H. F. et al., "Experimental and Clinical Data on Cyclabil," Acta Obstet Gynecol Scand, 1977, Suppl 65, pp. 39-43.
Theramex, "Estroprogestative Contraception Composition," Publication Date: Feb. 14, 2007, Retrieved from espacenet.com on May 28, 2010; English Abstract of EP 1 334 725.
G.B. Melis, et al., Contraception, "*A Comparative Study on the Efects of a Monophasic Pill Containing Desogestrel Plus 20 μg Ethinylestradiol, a Triphasic Combination Containing Levonorgestrel and a Monophasic Combination Containign gestrodene on Coagulatory Factors",* vol. 43, No. 1, pp. 23-30 (Jan. 1991), [including abstract].
A. R. Genazzani, et al. (Ed), Progress in Gynecology and Obstetrics, "*Multicenter Clinical Trial on the new Oral Contaceptive Containing 20 μg Ethinylestradiol",* Chapter 1, pp. 747-756, (1990).
PCT Search Report dated May 12, 1995.
Parke Davis package insert for Loestrin, Jun. 1993.

* cited by examiner

COMPOSITION FOR CONTRACEPTION

Matter enclosed in heavy brackets [ ] appears in the original patent but forms no part of this reissue specification; matter printed in italics indicates the additions made by reissue.

[This] *Notice: More than one reissue application has been filed for the reissue of U.S. Pat. No. 5,824,667: this Ser. No. 11/892,969 continuation reissue application is a divisional of reissue application Ser. No. 10/916,600 of Aug. 12, 2004 now abandoned, which is a continuation of reissue application Ser. No. 10/193,758 filed Jul. 12, 2002, now abandoned, which is a continuation of reissue application Ser. No. 09/504,084, filed Feb. 15, 2000, now U.S. Pat. No. Re. 37,838, which is a reissue of application Ser. No. 08/742,147, filed Oct. 31, 1996, now U.S. Pat. No. 5,824,667, which* is a continuation of the application Ser. No. 08/268,996 filed Jun. 30, 1994, now U.S. Pat. No. 5,583,129*; and reissue application Ser. No. 10/080,617, filed on Feb. 25, 2002, now U.S. Pat. No. Re. 38,253, is a continuation of reissue application Ser. No. 09/503,952, now U.S. Pat. No. Re. 37,564, which also is a reissue of application Ser. No. 08/742,147, filed Oct. 31, 1996, now U.S. Pat. No. 5,824,667, which is a continuation of the application Ser. No. 08/268,996, filed Jun. 30, 1994, now U.S. Pat. No. 5,583,129; and a continuation reissue application of Ser. No. 10/916,600 has been filed, on Mar. 24, 2006, having Ser. No. 11/388,172.*

DESCRIPTION

This invention relates to the common use of estrogens and gestagens for the production of a combination preparation for oral contraception and a corresponding pack containing this combination preparation.

Combination preparations for oral contraception are already known, for example, Femovan® [DE-PS 2 546 062] or Marvelon® [DE-OS 2 361 120]. These preparations consist of 21 active ingredient-containing (estrogen/gestagen) dosage units and 7 active ingredient-free coated tablets (sugar pills; placebos). The dose to be administered daily is uniformly high in each case (so-called single-phase preparations) and produces the desired contraceptive effect in the entire intake period and in the intake pause or during the intake of the placebos. In most preparations, a 7-day interruption of the intake of active ingredient-containing dosage units was considered necessary until quite recently to trigger a reliable withdrawal bleeding and thus to achieve a satisfactory cycle control.

Other preparations, which exhibit more than 21 dosage units containing an estrogenic and progestational active ingredient, and in which the intake pause is partially (Ijzerman, Pasquale) or completely (Kuhl) bridged over by estrogen-containing dosage units. In this case, it is possible that the synthetic estrogen ethinylestradiol otherwise contained in oral contraceptives is replaced partially or completely by a conjugated estrogen, preferably estradiol.

A combination preparation for substitution therapy and contraception for females before menopause (approximately starting from the 40th year of life) is known from EP-A-0 253 607. This combination preparation contains an estrogen from the group 17β-Estradiol,
ethinylestradiol and
mestranol as well as a gestagen from the group levonorgestrel,
gestodene,
desogestrel,
3-ketodesogestrel and
norethindrone.

A thus selected composition is to offset hormonal irregularities in the transition phase of premenopause and to help alleviate the symptoms caused by the hormonal changeover of the female organism in this phase. Such a composition simultaneously assures a premenopausal female the contraceptive protection still necessary at this age.

The development of new oral contraceptives for females of reproductive age before premenopause was characterized during the last twenty years above all by the reduction of the estrogen and gestagen dosages.

The reduction of the daily hormone dose was connected with the expectation to minimize the frequency of undesired side effects. Epidemiological data collected in the meantime confirm the desired trend toward better compatibility of lower-dosed preparations relative to cardiovascular complications [(1.) Thorogood, M., Oral Contraceptives and Cardiovascular Disease: An Epidemiologic Overview; Pharmacoepidemiology and Drug Safety, Vol. 2: 3-16 (1993); (2.) Gerstman, B. B.; Piper, J. M.; Tomita, D. K.; Ferguson, W. J.; Stadel, B. V.; Lundin, F. E.; Oral Contraceptive Estrogen Dose and the Risk of Deep Venous Thromboembolic Disease, Am. J. E., Vol. 133, No. 1, 32-36 (1991); (3.) Lidegaard, O., Oral contraception and risk of a cerebral thromboembolic attack: results of a case-control study; BMJ Vol. 306, 956-63 (1993); (4.) Vessey, M.; Mant, D.; Smith, A.; Yeates, D.; Oral contraceptives and venous thromboembolism: findings in a large prospective study; BMJ, Vol. 292, (1986); (5.) Mishell, D. R., Oral Contraception: Past, Present and Future Perspectives; Int. J. Fertil., 36 Suppl., 7-18 (1991)].

It is assumed that a correlation exists above all between the level of the estrogen dose and the incidence of cardiovascular diseases. But the maintenance of the contraceptive effectiveness stands in the way of an extreme reduction of the daily estrogen dose. Although the ovulation-inhibiting effect of the low-dosed oral contraceptives is caused mainly by the gestagenic component, the estrogenic component also makes a significant contribution to the central inhibition action and to the ovarian suppression (ovulation inhibition). Moreover, the daily estrogen dose must not fall below the minimum dose ranges, so that a satisfactory cycle control can be assured (Der Frauenarzt [The Gynecologist]; 34, 7: 793 (1993)].

The lowest estrogen dose contained in an oral contraceptive on the market at this time is 20 μg of ethinylestradiol, combined with 150 μg of desogestrel (Mercilon). Although the cycle control of this preparation is, as expected, somewhat poorer in comparison to preparations with a higher estrogen dose, the high acceptance rate of Mercilon indicates a small clinical relevance of this drawback. But the observation, made identically in several studies, of a lesser ovarial suppression of the preparation containing 20 μg of ethinylestradiol represents a clinically important problem. Obviously with this very low estrogen dose, in the case of many females, the maturation of follicles, which could be detected with ultrasonic studies or hormonal studies, results [(6.) Lunell, N. O.; Carlström, K.; Zador, G.; Ovulation inhibition with a combined oral contraceptive containing 20 μg of ethinylestradiol and 250 μg of levonorgestrel; Acta. Obstet. Gynecol. Scand. Suppl. 88: 17-21 (1979); (7.) Mall-Haefeli, M.; Werner-Zodrow, I.; Huber, P. R.; Klinische Erfahrungen mit Mercilon und Marvelon unter besonderer Berücksichtigung der Ovar-Funktion [Clinical Experience with Mercilon and Marvelon under special consideration of the ovary function]; Geburtsh. und Frauenheilk. [Obstetrics and Gynecology] 51, 35-38, Georg Thieme Verlag, Stuttgart-New York (1991); (8.) Strobel, E., Behandlung mit oralen Kontrazeptiva [Treatment with Oral Contraceptives]; Fortschr. Med. Vol. 110, No. 20 (1992); (9.) Letter to Editor, Contraception 45: 519-521 (1992); (10.) Teichmann, A. T.; Brill, K.; Can Dose Reduction of Ethinylestradiol in OCs Jeopardize Ovarian Suppression and Cycle Control? Abstract Book, VIIIth World Congress on Human Reproduction, Bali, Indonesia (1993)].

The hormone determinations performed showed that functional granulosa cells that secrete 17β-estradiol are involved. Each intake error in the case of females with clear ovarian activity, thus with follicular maturations, can result in a quick increase of gonadotropin production. The requirements for an ovulation would thus be present. It is estimated that approximately one third of females take oral contraceptives irregularly within one year of use (Gynpress, Volume 1, No. 3, 1990). The risk of a pregnancy is therefore high especially in the case of intake errors with the 20 μg ethinylestradiol preparations.

The object of this invention is an improved single-phase combination preparation for a female of reproductive age, who is not yet in premenopause, containing an estrogen and gestagen in each individual dosage unit, with the lowest possible estrogen content in each individual dosage unit, but also with a low total hormone content per administration cycle.

It has now been found that a pronounced ovarian suppression without frequent follicular maturations with low daily estrogen dosage, low total estrogen as well as low total hormone amount per administration cycle can be achieved by the use of a composition comprising an estrogen selected from 2.0 to 6.0 mg of 17β-estradiol and 0.015 to 0.020 mg of ethinylestradiol;

and a gestagen selected from 0.05 to 0.075 mg of gestodene, 0.075 to 0.125 mg of levonorgestrel, 0.06 to 0.15 mg of desogestrel, 0.06 to 0.15 mg of 3-ketodesogestrel,

[0.1 to 0.3] *1 to 3* mg of drospirenone,

[0.1 to 0.2] *1 to 2* mg of cyproterone acetate, 0.2 to 0.3 mg of norgestimate and >0.35 to 0.75 mg of norethisterone.

for the production of a form of dosage for contraception for a female of reproductive age, who has not yet reached premenopause, by administration of the form of dosage for 23 or 24 days, beginning on day one of the menstrual cycle (first day of menstrual bleeding), followed by 5 or 4 pill-free or sugar pill days, during a total of 28 days in the administration cycle.

The terms "premenopause" and "menopause" are used within the scope of this invention in the meaning of the conventional definition, see, for example, "The Controversial Climacteric," P. A. of Keep et al., Ed., MTP press (1981), e.g., p. 9.

The daily hormone dose is kept to a very low level here, while the usual 21-day intake is extended by two or three days. The remaining 5 or 4 days of a cycle are preferably bridged over by placebos, to avoid intake errors, or by 5 or 4 intake-free days.

According to a preferred embodiment of this invention, this relates to the use of a composition comprising an estrogen selected from >2.0 to 6.0 mg of 17β-estradiol and 0.020 mg of ethinylestradiol;

and a gestagen selected from

>0.06 to 0.075 mg of gestodene,

>0.100 to 0.125 mg of levonorgestrel,

>0.10 to 0.15 mg of desogestrel,

>0.10 to 0.15 mg of 3-ketodesogestrel,

[0.25 to 0.30] *2.5 to 3.0* mg of drospirenone,

[0.1 to 0.2] *1 to 2* mg of cyproterone acetate, 0.2 to 0.3. mg of norgestimate and 0.50 to 0.75 mg of norethisterone for the production of a form of dosage for contraception as described above.

In addition, this invention relates to a combination product for oral contraception, which comprises a) 23 or 24 dosage units, each containing an estrogen selected from >2.0 to 6.0 mg of 17β-estradiol and 0.020 mg of ethinylestradiol;

and a gestagen selected from

>0.06 to 0.075 mg of gestodene,

>0.100 to 0.125 mg of levonorgestrel,

>0.10 to 0.15 mg of desogestrel,

>0.10 to 0.15 mg of 3-ketodesogestrel,

[0.25 to 0.30] *2.5 to 3.0* mg of drospirenone,

[0.1 to 0.2] *1 to 2* mg of cyproterone acetate, 0.2 to 0.3 mg of norgestimate and 0.50 to 0.75 mg of norethisterone and b) 5 or 4 sugar pills or other indications to show that the daily administration of 23 or 24 dosage units is to be followed by 5 or 4 pill-free or sugar pill days are to be followed.

Further embodiments according to the invention follow from the features of the subclaims.

An especially preferred combination preparation according to this invention comprises 23 dosage units, each containing 20 μg of ethinylestradiol and 75 μg of gestodene and 5 sugar pills or other indications to show that no dosage unit or a sugar pill is administered during the last 5 days of the menstrual cycle.

The clinical study briefly described below was performed with ethinylestradiol as estrogen and gestodene as representative of the substance class of the gestagens possible according to the invention. All possible combinations of ethinylestradiol or estradiol according to the invention in the indicated dosages with one of the selected gestagens in the indicated dosages as 23- or 24-day preparations exhibit the advantages according to the invention.

The 23-day administration of 20 μg of ethinylestradiol in combination with 75 μg of gestodene results, in comparison to the 21-day administration, in a stronger ovarian suppression. In a double-placebo, randomized study on healthy females with normal ovarian function, groups of 30 test subjects each received the combination preparation either once daily over 21 or 23 days as well as placebos on 7 or 5 days (to assure the double-placebo nature of the study).

The treatment began after an ovulatory, untreated preliminary cycle on the first day of the menstrual bleeding of the subsequent cycle and extended altogether over three treatment cycles. The study was concluded with an untreated follow-up cycle.

The ovarian suppression was measured based on the level of the endogenous 17β-estradiol level and the size of follicular structures. The results show that the 17β-estradiol levels with 23-day intake of the test preparation were significantly lower ($p<0.05$) in comparison to the 21-day administration (FIG. 1).

In accordance with this finding, the number of females with follicular maturations was also clearly higher in the 21-time administration relative to the 23-time administration (FIG. 2).

The intake interval extended only by two days surprisingly produces a significantly greater ovarian suppression with unchangingly low daily doses. The combination preparation according to the invention thus achieves the effectiveness previously known for preparations with a daily content of 30 μg of ethinylestradiol, although the daily ethinylestradiol dose is 33% lower and also the total dose per cycle is 27% lower.

The advantages of a combination preparation for oral contraception to be administered over 23 days relative to the usual 21-day preparations with less than 30 μg of ethinylestradiol can be characterized as follows:

1. A significantly lower frequency of follicular developments in the user (maximum of 13% in females who received the 23-day preparation relative to a maximum of 40% among those who received the 21-day preparation). This means a greater contraceptive reliability of the 23-day preparation, especially in the case of previous intake errors. The danger of "breakthrough ovulations" is smaller.

2. The occurrence of large follicles of more than a 30 mm diameter is extremely rare. The development of ovarian cysts is improbable with the 23-day preparation in comparison to the 21-day preparation.

3. The recruitment of dominant follicles is suppressed in the shortened intake-free pause.

4. The endogenous 17β-estradiol levels are suppressed easily controllably in the case of the majority of the users of the 23-day preparation. Clinical symptoms such as breast tenseness, premenstrual syndrome and menstrual disorders, which can be attributed to increased and greatly fluctuating estrogen levels, are observed with the 23-day preparation with clearly lower frequency.

In summary, an intake, extended by two (or three) days, of preparations containing 20 μg of ethinylestradiol in each daily dosage unit can produce the above-mentioned advantages, without the daily dose having to be raised to the previously largely used level of 30 μg of ethinylestradiol.

The formulation of an estrogen and gestagen for the use according to the invention or for a combination preparation according to the invention takes place completely analogously as it is already known for usual oral contraceptives with 21-day intake period of the active ingredients, such as, for example, Femovan® (ethinylestradiol/gestodene) or Microgynon® (ethinylestradiol/levonorgestrel).

A pack containing a combination preparation according to the invention is also designed analogously to packs for already known oral contraceptives on the market with the variation that instead of the usual 21 dosage units containing the active components, now 23 or 24 such dosage units and 5 or 4 sugar pills are present or else contain other suitable indications that 5 or 4 days are to be bridged over until continuation of the intake of active ingredient-containing dosage units.

Moreover, reference is made to the statements made in EP-A 0 253 607, especially also to the statements there for determination of equivalent amounts of ethinylestradiol and 17β-estradiol, on the one hand, and various gestagens, such as levonorgestrel, desogestrel, 3-ketodesogestrel and gestodene, on the other hand.

For further details for the determination of dose equivalents of various gestagenic active ingredients, reference is made to "Probleme der Dosisfindung: Sexualhormone" [Problems of Dose-Finding: Sex Hormones]; F. Neumann et al. in "Arzneimittelforschung" (Pharmaceutical Agent Research) 27, 2a, 296-318 (1977), as well as to "Aktuelle Entwicklungen in der hormonalen Kontrazeption" [Current Developments in Hormonal Contraception]; H. Kuhl in Gynäkologe" [Gynecologist) 25: 231-240 (1992).

Figure 1:
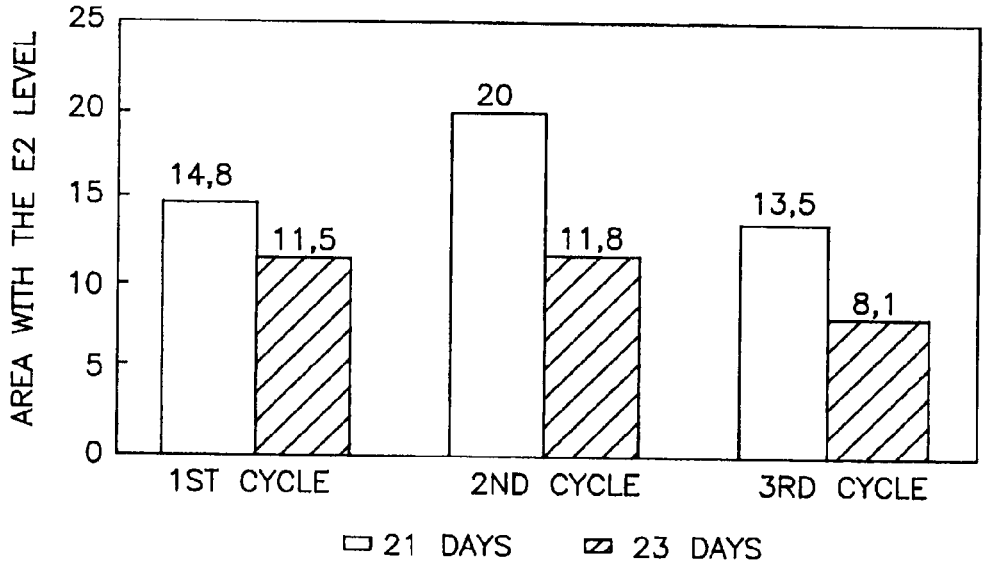
FIG. 1: Area with the 17β-estradiol level in groups of 30 females, who are treated with an oral contraceptive (75 μg of gestodene+20 μg of ethinylestradiol) in 21- or 23-day administration interval over three cycles.
Figure 2:
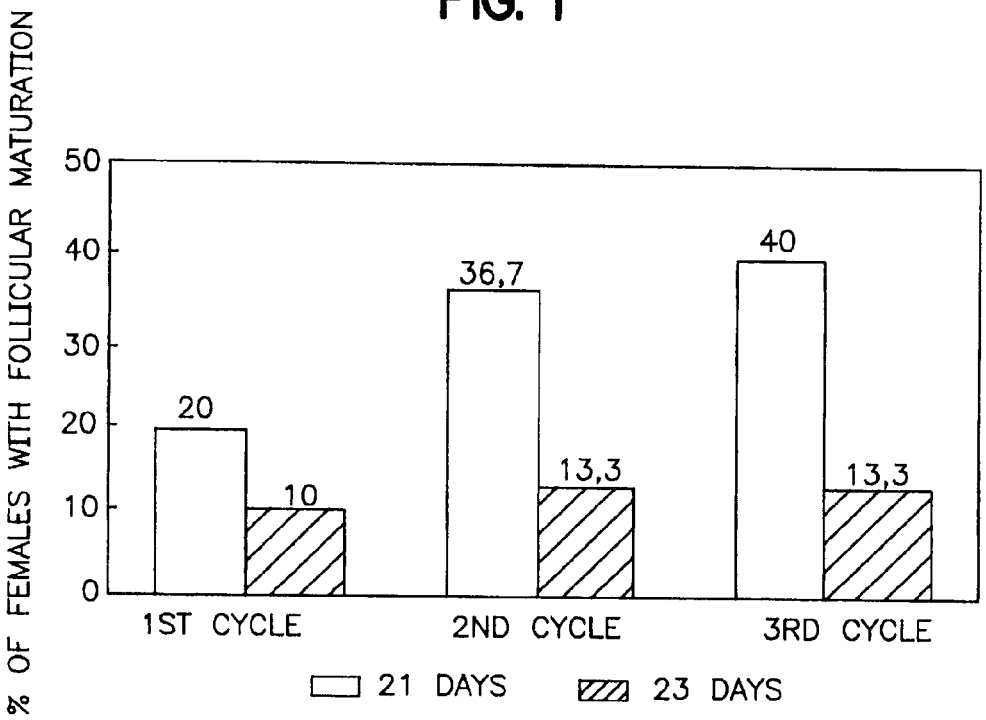
FIG. 2: Number of females in %, who showed follicular developments (>13 mm diameter) with 21- or 23-day treatment with an oral contraceptive (75 μg of gestodene+20 μg of ethinylestradiol).

We claim:

[1. A combination product for oral contraception, comprising (a) 23 or 24 dosage units, each containing an estrogen selected from
>2.0 to 6.0 mg of 17β-estradiol and
0.020 mg of ethinylestradiol;

and a gestagen selected from
0.25 to 0.30 mg of drospirenone and
0.1 to 0.2 mg of cyproterone acetate, and b) 5 or 4, respectively, active ingredient-free placebo pills or other indications to show that the daily administration of the 23 or 24 dosage units respectively, is to be followed by 5 or 4, respectively pill-free or placebo pill days.]

[2. A combination preparation for oral contraception according to claim 1, wherein the estrogen is ethinylestradiol.]

[3. A combination preparation of claim 2, wherein the gestagen is cyproterone acetate.]

[4. A combination preparation of claim 2, wherein the gestagen is drospirenone.]

[5. A combination preparation according to claim 1, wherein the estrogen is present in a dose of 20 μg of ethinylestradiol or an equivalent dose of 17β-estradiol and the gestagen is present in a dose equivalent to 75 μg of gestadene.]

[6. A combination preparation according to claim 1, which comprises 23 dosage units and 5 placebo pills or other indications to show that no dosage unit or a placebo pill is administered during the last 5 days of the menstrual cycle.]

[7. A combination preparation according to claim 1, which comprises 23 dosage units, each containing 20 μg of ethinylestradiol and a dose of cyproterone acetate or drospirenone equivalent to 75 μg of gestodene and 5 placebo pills or other indications to show that no dosage unit or a placebo pill is administered during the last 5 days of the menstrual cycle.]

[8. A combination preparation of claim 1, wherein the estrogen is 17β-estradiol.]

[9. A combination preparation of claim 8, wherein the gestagen is cyproterone acetate.]

[10. A combination preparation of claim 8, wherein the gestagen is drospirenone.]

*11. A method of inducing contraception in a female of reproductive age who has not yet reached premenopause, comprising administering to said female a monophasic composition that effectively lessens premenstrual syndrome, com-*

*prising 0.015 to 0.020 mg of ethynylestradiol and 1-3 mg of drospirenone, wherein the composition is administered for 23 or 24 days, beginning on day one of the menstrual cycle, followed by 5 or 4 pill-free or sugar pill days, during a total of 28 days in the administration cycle.*

*12. A method of claim 11 wherein the amount of ethynylestradiol is 0.020 mg and the amount of drospirenone is 3 mg.*

*13. A method of claim 12 wherein the composition is administered for 24 days, beginning on day one of the menstrual cycle, followed by 4 pill-free or sugar pill days, during a total of 28 days in the administration cycle.*

*14. A method of inducing contraception in a female of reproductive age who has not yet reached premenopause, comprising administering to said female a monophasic composition that effectively lessens breast tenderness, comprising 0.015 to 0.020 mg of ethynylestradiol and 1-3 mg of drospirenone, wherein the composition effectively lessens breast tenderness, and is administered for 23 or 24 days, beginning on day one of the menstrual cycle, followed by 5 or 4 pill-free or sugar pill days, during a total of 28 days in the administration cycle.*

*15. A method of claim 14 wherein the amount of ethynylestradiol is 0.020 mg and the amount of drospirenone is 3 mg.*

*16. A method of claim 15 wherein the composition is administered for 24 days, beginning on day one of the menstrual cycle, followed by 4 pill-free or sugar pill days, during a total of 28 days in the administration cycle.*

*17. A method of claim 11 wherein the composition effectively lessens breast tenderness.*

*18. A method of claim 17 wherein the amount of ethynylestradiol is 0.020 mg and the amount of drospirenone is 3 mg.*

*19. A method of claim 18 wherein the composition is administered for 24 days, beginning on day one of the menstrual cycle, followed by 4 pill-free or sugar pill days, during a total of 28 days in the administration cycle.*

*20. A method of inducing contraception in a female of reproductive age suffering from premenstrual syndrome who has not yet reached premenopause, comprising administering to said female a monophasic composition comprising 0.015 to 0.020 mg of ethynylestradiol and 1-3 mg of drospirenone, wherein the composition is administered for 23 or 24 days, beginning on day one of the menstrual cycle, followed by 5 or 4 pill-free or sugar pill days, during a total of 28 days in the administration cycle.*

*21. A method of claim 20 wherein the amount of ethynylestradiol is 0.020 mg and the amount of drospirenone is 3 mg.*

*22. A method of claim 21 wherein the composition is administered for 24 days, beginning on day one of the menstrual cycle, followed by 4 pill-free or sugar pill days, during a total of 28 days in the administration cycle.*

*23. A method of inducing contraception in a female of reproductive age suffering from breast tenderness who has not yet reached premenopause, comprising administering to said female a monophasic composition comprising 0.015 to 0.020 mg of ethynylestradiol and 1-3 mg of drospirenone, wherein the composition is administered for 23 or 24 days, beginning on day one of the menstrual cycle, followed by 5 or 4 pill-free or sugar pill days, during a total of 28 days in the administration cycle.*

*24. A method of claim 23 wherein the amount of ethynylestradiol is 0.020 mg and the amount of drospirenone is 3 mg.*

*25. A method of claim 24 wherein the composition is administered for 24 days, beginning on day one of the menstrual cycle, followed by 4 pill-free or sugar pill days, during a total of 28 days in the administration cycle.*

*26. A method of claim 20 wherein the female of reproductive age suffers from breast tenderness.*

*27. A method of claim 26 wherein the amount of ethynylestradiol is 0.020 mg and the amount of drospirenone is 3 mg.*

*28. A method of claim 27 wherein the composition is administered for 24 days, beginning on day one of the menstrual cycle, followed by 4 pill-free or sugar pill days, during a total of 28 days in the administration cycle.*

* * * * *

UNITED STATES PATENT AND TRADEMARK OFFICE

CERTIFICATE OF CORRECTION

PATENT NO. : RE44,159 E
APPLICATION NO. : 11/892969
DATED : April 16, 2013
INVENTOR(S) : Jurgen Spona It is certified that error appears in the above-identified patent and that said Letters Patent is hereby corrected as shown below:

TITLE PAGE

Item (60) U.S. Applications, reads as follows:

-- Division of application No. 10/916,600, filed on Aug. 12, 2004, now abandoned, which is a continuation of application No. 10/193,758, filed on Jul. 12, 2002, now abandoned, which is a continuation of application No. 09/504,084, filed on Feb. 15, 2000, now Pat. No. Re. 37,838, which is a continuation of application No. 08/268,996, filed on Jun. 30, 1994, now Pat. No. 5,583, 129, application No. 11/892,969, which is a continuation of application No. 09/503,952, filed on Feb. 15, 2000, now Pat. No. Re. 37,564, which is a continuation of application No. 08/268,996, filed on Jun. 30, 1994, now Pat. No. 5,583,129. --

Should read:

-- More than one reissue application has been filed for the reissue of U.S. Patent No. 5,824,667: this Serial No. 11/892,969 continuation reissue application is a divisional of reissue application Serial No. 10/916,600 of August 12, 2004, now abandoned, which is a continuation of reissue application Serial No. 10/193,758, filed July 12, 2002, now abandoned, which is a continuation of reissue application Serial No. 09/504,084, filed February 15, 2000, now U.S. Patent No. Re. 37,838, which is a reissue of application Serial No. 08/742,147, filed October 31, 1996, now U.S. Patent No. 5,824,667, which is a continuation of the application Serial No. 08/268,996, filed June 30, 1994, now U.S. Patent No. 5,583,129; and reissue application Serial No. 10/080,617, filed on February 25, 2002, now U.S. Patent No. Re. 38,253, is a continuation of reissue application Serial No 09/503,952, now U.S. Patent No. Re. 37,564, which also is a reissue of application Serial No. 08/742,147, filed October 31, 1996, now U.S. Patent No. 5,824,667, which is a continuation of the application Serial No. 08/268,996, filed Signed and Sealed this
Thirty-first Day of December, 2013

Margaret A. Focarino

Margaret A. Focarino
*Commissioner for Patents of the United States Patent and Trademark Office*

June 30, 1994, now U.S. Patent No. 5,583,129; and a continuation reissue application of Serial No. 10/916,600 has been filed, on March 24, 2006, having Serial No. 11/388,172. --